United States Patent [19]

Datta et al.

[11] Patent Number: 5,168,055

[45] Date of Patent: * Dec. 1, 1992

[54] FERMENTATION AND PURIFICATION PROCESS FOR SUCCINIC ACID

[76] Inventors: Rathin Datta, 442 W. Melrose Ave., #3, Chicago, Ill. 60657; David A. Glassner, 4454 Satinwood Rd., Okemos, Mich. 48864; Mahendra K. Jain, 3950 Jonquil La., Okemos, Mich. 48864; John R. Vick Roy, 1642 Seven Trails Ct., Okemos, Mich. 48864

[*] Notice: The portion of the term of this patent subsequent to Apr. 1, 2009 has been disclaimed.

[21] Appl. No.: 372,721

[22] Filed: Jun. 28, 1989

Related U.S. Application Data

[63] Continuation-in-part of Ser. No. 325,404, Mar. 17, 1989, which is a continuation-in-part of Ser. No. 301,788, Jan. 25, 1989, which is a continuation-in-part of Ser. No. 873,031, Jun. 11, 1986, abandoned.

[51] Int. Cl.$^5$ .......................... C12P 7/46; C12N 1/20; C07C 51/42
[52] U.S. Cl. .................................. 435/145; 435/252.1; 435/170; 562/593; 562/590
[58] Field of Search ............ 435/144, 145, 822, 252.1, 435/170; 562/593, 590

[56] References Cited

U.S. PATENT DOCUMENTS 4,110,175  8/1978  Ahlgren et al. ................. 204/180 B
4,678,553  7/1987  Mandle et al. ................... 204/182.6
4,766,161  8/1988  Chlanda et al. ..................... 521/27

FOREIGN PATENT DOCUMENTS 0249773  12/1987  European Pat. Off. ............ 435/145
8318631   5/1985  France .

OTHER PUBLICATIONS

Gerhardt et al., Manual of Methods for General Bacteriology, ASM, 1981, pp. 67-69.
The Merck Index, 1983, 10th ed., p. 234.
Bergey's Manual of Systematic Bacteriology, Krieg et al., ed. 1984 pp. 704-705.
Dellweg (I)-*Biotechnology*, vol. 3, 1983 pp. 442-444.
Dellweg (II)-*Biotechnology*, vol. 3, 1983 pp. 414-417.
Hongo, M., Nomura, Y. and M. Iwahara, "Novel Method of Lactic Acid Production by Electrodialysis Fermentation," Appl. Environ, Microbiol. 52, 2, 314-319, Aug. 1986.
Nomura, Y., Iwahara, M. and M. Hongo, "Lactic Acid Production by Electrodialysis Fermentation Using Immobilized Growing Cells," Biotechnol. & Bioeng. 30, 788-793, Oct. 1987.
Caspari et al., Arch Microbiol., vol. 135, pp. 16-24 (1983).
Davis et al., Int. J. Syst. Bacteriol., vol. 26, pp. 498-504 (1976).
"Aquatech" system, Product Brochure, Allied Signal Corporation, 1985.
Hopgood et al., Aust. J. Biol. Sci., vol. 20, pp. 165-192 (1967).
Caldwell et al., J. Bacteriol., vol. 98, pp. 668-676 (1969).

*Primary Examiner*—Irene Marx
*Attorney, Agent, or Firm*—Quarles & Brady

[57] ABSTRACT

A process for economically producing highly purified succinic acid comprises growing a succinate-producing microorganism on a low cost carbohydrate substrate; simultaneously neutralizing the fermentation broth and precipitating the succinate as calcium succinate by adding a calcium ion source to form calcium succinate; isolating the calcium succinate; slurrying the calcium succinate in water and treating it with sulfuric acid to form calcium sulfate and succinic acid; and then treating the succinic acid with first a strongly acidic ion exchanger and then a weakly basic ion exchanger to remove impurities and obtain a highly purified succinic acid product. In a preferred embodiment, the calcium succinate is isolated from the fermentation broth by filtration; the filtrate is heated to precipitate additional calcium succinate; and, the spent filtrate which contains nutrients is recycled to the fermentor.

7 Claims, 1 Drawing Sheet

FIG. 1

000# FERMENTATION AND PURIFICATION PROCESS FOR SUCCINIC ACID

RELATED CASES

This application is a continuation-in-part of earlier copending applications U.S. patent Ser. No. 07/325,404 filed Mar. 17, 1989, which is a continuation-in-part of U.S. patent Ser. No. 07/301,788, filed Jan. 25, 1989, which is a continuation-in-part of U.S. patent Ser. No. 873,031, filed Jun. 11, 1986, now abandoned.

FIELD OF THE INVENTION

The present invention relates to an improved process for the production of succinic acid by fermentation of carbohydrate to form a succinate salt, the subsequent conversion of the succinate salt to succinic acid, and the purification of the succinic acid.

BACKGROUND OF THE INVENTION

Succinic acid and its derivatives are widely used as a specialty chemical for applications in polymers, foods, pharmaceuticals, and cosmetics. Furthermore, succinic acid is a valuable 4-carbon intermediate useful for the production of 1,4-butanediol, tetrahydrofuran, and gammabutyrolactone.

Although the succinate ion is a common intermediate in the metabolic pathway of several anaerobic microorganisms, there are no published examples of any fermentation that produces succinate in large amounts or with high yields. For example, succinate is a key intermediate for anaerobic fermentations by propionate-producing bacteria, but it is only produced in low yields and in low concentrations.

Succinate is also produced by anaerobic rumen bacteria These bacteria include *Bacteroides ruminicola* whose growth and metabolism is described by Howlett et al. (1976) and *Bacteroides amylophilus* whose culture and growth are described by Caldwell et al. *J. Bacteriol.*, 98, 668–76 (1969) and Hamlin et al. *J. Bacteriol.*, 72, 548–54 (1956).

Although the rumen bacteria give higher yields of succinate than do the propionate-producing bacteria, the reported fermentations were run in very dilute solutions and gave a variety of products in generally low yields. Moreover, the rumen organisms tend to lyse after a comparatively short fermentation time, thereby leading to unstable fermentations.

Anderson and Ordal described in *J. Bacteriol.*, 81, 139 (1969) the isolation of a facultative anaerobe, *Cytophaga succinicans*, which produced succinate, acetate, and formate from dextrose with fixation of carbon dioxide. However, this organism produced succinate in such low concentrations that it would not be economically feasible to recover succinic acid from the fermentation medium. Similar results were observed with the Bacteriodes fragilis obtained from the gastrointestinal tract (Caspari et al., *Arch. Microbiol.*, 135, 16–24 (1983).

In order to develop a commercially attractive process to produce succinic acid by fermentation, several important fermentation and product purification criteria need to be accomplished. The fermentation should be high yield (wt %) and produce a high product concentration using inexpensive raw materials and nutrients. Since anaerobic fermentations are run at neutral or near neutral pHs, salts of organic acids rather than the acids themselves are produced. The fermentation broth also contains cells, protein and other undesirable materials. The desired product from the process is the purified acid which can be used for specialty or commodity chemical manufacture. Hence, to be commercially viable, a high yielding, economical fermentation process has to be integrated with an efficient recovery and purification process.

We have previously demonstrated that *Anaerobiospirillum succiniciproducens* (ATCC 53488) produces enough succinate to allow simultaneous fermentation and calcium succinate precipitation under strictly controlled conditions and when the correct calcium salt is used for neutralization. However, for an economic process, the fermentation should use low cost nutrients, have high yield, high productivity, recycle nutrients and the recovery of the precipitated calcium succinate. Furthermore, the recovery of dissolved succinate from the filtrate is desirable. In addition, the succinate obtained must then be economically converted to high purity succinic acid.

BRIEF DESCRIPTION OF THE PRESENT INVENTION

It is the primary object of the present invention to disclose a novel process for producing succinate by fermentation, converting the succinate to succinic acid and purifying the succinic acid to obtain a highly purified product.

In the practice of the present invention, an inexpensive carbohydrate-containing substrate is fermented with a succinate-producing microorganism under carefully controlled conditions and neutralized with Ca(OH)$_2$ or calcium oxide, to simultaneously precipitate the succinate as calcium succinate in the fermentor. The slurry is filtered to remove the precipitated succinate. The filtrate is heated to about 70°–95° C. and further precipitation of calcium succinate is achieved The filtered calcium succinate is slurried with water and enough concentrated sulfuric acid slowly added to convert the calcium succinate to succinic acid and an insoluble calcium sulfate (gypsum) which precipitates. The calcium sulfate is removed by filtration. The filtrate which contains the succinic acid, any residual cations and anions and nitrogenous materials is then contacted first with a strongly acidic cation exchange resin in the free acid form which removes calcium and other cation impurities and then with a weakly basic anion exchange resin in the free base form which removes sulfate and strong anionic contaminants without removing the succinic acid. The product obtained is a highly purified succinic acid containing less than 1% nitrogenous impurities and less than 5 ppm of sulfate, which is especially useful for commercial applications.

BRIEF DESCRIPTION OF THE DRAWINGS

In the drawings a schematic flow diagram of the process of the present invention is shown in FIG. 1.

DESCRIPTION OF THE PREFERRED EMBODIMENT

In the preferred practice of the present invention, a culture of *A. succiniciproducens* (ATCC 53488) is anaerobically grown at a controlled pH between about 5.8 to about 6.6 in a fermentor with a medium containing carbohydrates; other nutrients, such as corn steep liquor; tryptophan; and, sodium ions under a partial pressure of at least about 0.1 atmosphere $CO_2$ until a yield of about 75 weight percent of succinate salt based on the weight of the carbohydrate is obtained and the fermentation broth contains at least about 20 g/l of succinate.

The preferred strain ferments carbohydrate in a media containing high (6-10 g/l initial concentration) acetate concentrations giving high productivity (2-6 g/l hr) and high concentrations (40-80 g/l) of succinate. As a result, it is possible to successfully precipitate a calcium succinate product in the fermentor during the fermentation by using calcium hydroxide or calcium oxide for neutralization. The preferred fermentation and precipitation processes allow the concentration and purification of a dilute product using filtration. The precipitate has favorable filtration characteristics giving a high filtration rate (20–50 gal/hr ft$^2$). Batch, fed batch, and continuous fermentor configuration all can be successfully used for the simultaneous fermentation and calcium succinate product precipitation.

The filtrate thus obtained is heated to about 70° to about 95° C. and to precipitate additional calcium succinate and refiltered. The heated filtrate may be seeded with calcium succinate if required. The filtrate which contains dissolved nutrients is preferably recycled to the fermentor.

The desired succinic acid product is recovered from the precipitated calcium succinate by acidification of the succinate with sulfuric acid followed by filtration to remove the calcium sulfate (gypsum) which precipitates. The filtrate thus obtained is a concentrated aqueous succinic acid stream (150-300 g/l).

The acidification of the calcium succinate is accomplished by slurrying the calcium succinate with water, preferably about 33% w/v, adding excess sulfuric acid to precipitate the calcium sulfate, followed by a careful neutralization of the excess acid with calcium hydroxide. The filter cake of calcium sulfate is washed with a volume of hot water equal to the volume of solution contained by the filter cake to remove all the succinic acid from the filter cake.

The succinic acid aqueous stream (filtrate) also contains calcium and other cations, sulfate and other anions and nitrogeneous materials after the calcium sulfate removal. Since some of these impurities in the succinic acid stream are ionic in nature, it is unexpected to discover that the impurities can be removed without removing the succinic acid itself.

In the preferred embodiment of the inventive process, the succinic acid aqueous stream is first treated with a cation exchanger (such as DOWEX 50 WX8), having the ability to remove positively charged ions, and then with a weakly basic anion exchanger (such as Rohm and Haas Amberlite IRA-94) which has the ability to remove negatively charged ions without removing the succinic acid which itself is an ionized product which could be lost in the ion exchange process. The proper selection of the types of ion exchange resins used, order of use, and operating parameters are all necessary to remove the impurities from the succinic acid aqueous stream without removing the succinic acid. This treatment also removes some contaminating nitrogenous impurities (proteins and amino acids).

The result is a low cost, high purity, succinic acid product which contains low concentrations of impurities. The final product preferably will contain about 80 to about 99% succinic acid, on a dry basis, less then 1% nitrogenous impurities and less then 10 ppm of sulfate ions or other contaminating ions.

The carbohydrate used in the fermentation can be any carbohydrate that is fermented by the strain of bacterium used. For *A. succiniciproducens*, suitable carbohydrate sources include dextrose, sucrose, fructose, lactose, soluble starches, and corn syrups. The fermentation is conducted in an aqueous medium containing tryptophan, sodium ions and dissolved carbon dioxide. Other nutrients and growth factors needed for the growth and the reproduction of the microorganism employed also may be added to the medium.

The concentration of carbohydrate in the medium is between about 20 g/l to about 100 g/l, preferably between about 40 g/l and about 80 g/l. Carbohydrate concentrations above about 100 g/l give solutions with such high osmotic pressures that the organisms do not grow well. Although the organisms will grow in solutions containing less than 20 g carbohydrate per liter, the concentration of product is so low that its recovery usually is not practical.

Carbon dioxide can be supplied to the fermentation medium in various ways. The medium can be sparged with $CO_2$ gas. The fermentation can be run in a pressurized reactor which contains carbon dioxide at superatmospheric pressure. The $CO_2$ can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The medium should contain dissolved $CO_2$ in equilibrium with a minimum of about 0.1 atmosphere partial pressure of carbon dioxide. In the preferred embodiment, the medium is saturated with carbon dioxide and the atmosphere contains about 0.3 atmosphere partial pressure of carbon dioxide or higher.

In order to obtain good production of succinate salt, the pH of the medium is maintained in the range of from about 5.8 to about 6.6. At higher pH values, the main product is lactate rather than succinate, while at lower pH values, the fermentation is inhibited. The pH is conveniently maintained by the addition of calcium carbonate, calcium oxide or calcium hydroxide, or mixtures thereof.

The fermentation process of this invention is carried out at a temperature between about 25° C. and about 45° C. Optimum growth of the *A. succiniciproducens* organism is about 39° C. Since the preferred organism is a strict anaerobe, fermentations using the organism are carried out under anaerobic conditions in a medium which has been sterilized by heat or other means well known in the fermentation art.

The following are important features of the preferred embodiment of the process of the present invention:
  it uses a low cost fermentation media
  it employs fermentation operating parameters which give high yield and high productivity and permit the simultaneous precipitation of calcium succinate
  it can provide for the recycle of spent filtrate to increase fermentation productivity and overall product yield
  it uses filtration to concentrate and recover succinate from the fermentor as calcium succinate
  it employs acidification of the calcium succinate solids followed by removal of the calcium sulfate by filtration to yield a succinic acid stream
  it utilizes a unique set and arrangement of ion exchangers to remove ionic impurities.

The practice of the invention is further illustrated by the Examples.

GENERAL DESCRIPTION OF MATERIALS AND METHODS EMPLOYED IN EXAMPLES

Fermentation Media and Conditions

Fermentations using *A. succiniciproducens* (ATCC 53488) were conducted in a low cost media which, unless otherwise specified, contained: commercial grade dextrose, 50 g/L (Corn Products "Cerelose", or equivalent) and corn steep liquor, 10 g/L (dry basis) (Corn Products "Argo E801" or equivalent commercial grade). After sterilization, the media was cooled to 39° C. as 100% $CO_2$ (AIRCO, Murray Hill, N.J., Industrial Grade or equivalent) was sparged through the fermentor. The pH was adjusted to 6.4 by adding 3M $Na_2CO_3$ (approximately 10 ml/L) unless otherwise specified. Twenty-five ppm of filter sterilized tryptophan was added to the media before it was reduced by adding 0.125 g/L cysteine hydrochloride. Fermentations were conducted at 38±1° C. in a gas phase of 1.0 atm $CO_2$ and pH controlled between 6.0 to 6.3 using a 25 wt% slurry of high purity industrial grade lime (Mississippi Lime Co., pulverized grade, or equivalent).

Precipitated calcium succinate solids from the fermentation broth were recovered by filtration. The filtrate was then heated to 80° C. for 15 min to precipitate additional calcium succinate which was recovered by filtration.

*A. succiniciproducens* fermentations of carbohydrates were conducted in batch, fed-batch, and continuous fermentations in 1-2 liter fermentors. Fermentations were scaled-up to 80 liter volume to prove the scalability of the process without affecting the yield and productivity. Recycling of spent filtrate was done in 2-liter batch fermentations.

The batch and fed-batch fermentations were conducted in 2-liter "Multigen" fermentors (New Brunswick Scientific Co., Edison, N.J.). The fermentors were equipped with a "Chemcadet" or Model 5997-30 pH meter/controller and an Ismatec peristaltic pump (Cole Parmer Instrument Co., Chicago, Ill.). 80 liter fermentations were conducted in a 'Mobile Pilot Plant' New Brunswick Model MPPF 80L (New Brunswick Scientific Co., Edison, N.J.).

Multistage continuous fermentations were conducted using 1- and 2-liter New Brunswick Scientific Co. "Multigen" fermentors. The two stage continuous fermentations were conducted with a working volume of 375 ml for stage 1 and 1400 ml for stage 2. The feed media was pumped into stage 1 by a peristaltic pump. The effluent of stage 1 was pumped into stage 2 using another peristaltic pump. The effluent from stage 2 was collected in an effluent holding tank. The fermentations were conducted at pH 5.9-6.0 in the first stage and at pH 6.1 to 6.3 in the second stage. The pH was controlled by 40 wt% calcium hydroxide slurry on demand. The carbon dioxide gas was supplied to the fermentor headspace by continuous flow. The media contained corn steep liquor, $Na_2CO_3$, tryptophan, and dextrose in solution and was gassed with 100% $CO_2$. The media was reduced with cysteine HCl (0.25 g/l). The first stage, was inoculated with 5% V/V inoculum and was allowed to begin growth in batch conditions. Flow through the fermentors was begun once growth was established. The pH in both fermentors was controlled using "Chemcadet" pH controllers. Agitation was controlled between 100-200 rpm.

The precipitated calcium succinate was filtered at 39° C. by vacuum filtration. Broths from 1L and 2 L fermentations were filtered using Whatman No. 1 filter paper (Whatman Inc., Clifton Heights, N.J.) in a 17 cm dia. ceramic Buchner funnel. The filtrate was collected in a 2 L Pyrex vacuum flask. The filter cake was washed with the minimum volume required to remove all the filtrate. For larger fermentations a 20-ounce cotton twill filter cloth in a 12-inch diameter Buchner funnel was used for the filtration. The filtrate was then heated to 80° C., seeded with calcium succinate and mixed for 15 minutes allowing equilibrium to be established. The hot slurry was then filtered. The calcium succinate filter cake was washed with enough 80° C. water to remove all filtrate.

Conversion to Succinic Acid

The washed calcium succinate cake was reslurried to 33% w/v solids with water. Concentrated sulfuric acid was slowly added, in 10% excess of the amount required to convert all of the calcium succinate to succinic acid. This slurry was mixed well and allowed to react completely. Then the resulting mixture of calcium sulfate (gypsum) solids and succinic acid solution was heated to 80° C. and vacuum filtered through 20-ounce cotton twill filter cloth. The filter cake was washed with enough 80° C. water to remove all the succinic acid.

Purification of the Succinic Acid

After calcium sulfate (gypsum) filtration, residual cations, anions, and nitrogenous materials still remained in the succinic acid filtrate. A strongly acidic cation exchange resin, in the acid form, such as Dowex 50WX8 (Dow Chemical Co., Midland, Mich.), was used to remove the calcium and other cation impurities. The solution was then treated with a weakly basic anion exchange resin in the free base form, such as Amberlite IRA-94 (Rohm & Haas Co., Philadelphia, Pa.), which removes sulfate and other strong anionic contaminants without removing the succinic acid.

Two-inch diameter glass columns were used for ion-exchange purification of the succinic acid stream. The succinic acid stream was treated continuously in the columns at flow rates of 5-10 bed volumes per hour. Columns were regenerated using dilute (1-2M) sodium hydroxide or hydrochloric acid, as appropriate.

Analytical Methods

The organic acid fermentation products were determined using high-performance liquid chromatography (HPLC) as described by Guerrant et al., J. Clinical Microbiol., v. 16 (2), 355 (1982). Components were analyzed chromatographically by elution with 0.006 N $H_2SO_4$ from a cation-exchange resin in the hydrogen form. A Waters Model 60 HPLC system with a Bio-Rad HPX-87H column and a Waters Model 410 Refractive Index detector were used in this analysis. The carbohydrate was determined by a YSI dextrose analyzer (Yellow Springs Instrument Company, Yellow Springs, Ohio). All the results were reported as grams per liter.

Total Kjeldahl nitrogen (TKN) was determined using a Tectator Model 1030 Kjeldahl system and protein was calculated by multiplying %TKN by 6.25. Calcium was determined spectrophotometrically as per Sigma Chemical Co. test kit #587-A using Bausch & Lomb Spectronic-20 Spectrophotometer (Milton-Roy Co., Rochester, N.J.). Sulfate determinations were made gravimetrically by the barium precipitation method of Fronson, M. A., ed., *Standard Methods* (16th), *Amer. Chem. Soc.*, 464 (1985).

EXAMPLES

Fermentations were conducted in 2-liter New Brunswick Multigen Fermentors at different pH values, $CO_2$ concentrations and with and without sodium ions and tryptophan additions. These fermentations were neutralized with 25 wt % calcium hydroxide slurry.

EXAMPLES 1 and 2

Table 1 summarizes the comparative results obtained when fermentations were run at two different pH values, pH 6.1 and 6.8. The fermentors were gassed with 100% $CO_2$ at a rate of 10 ml/min. Fermentation media was supplemented with 25 ppm tryptophan. As can be seen in Table 1, the fermentation product spectrum is different at these two pH's. Lactate is the major product when the fermentation is carried out at pH 6.8. At pH 6.1 the major fermentation product is succinate with a yield of 87 wt %. Under these conditions, acetate is always produced as a major by-product. The organism did not grow or consume substrate at a pH of 5.5 or lower. The results show that fermentations need to be conducted at pH between 5.8 and 6.6 to obtain high succinate yield. The succinate yield based on dextrose consumption at optimum fermentation pH is 87-90 wt %.

TABLE 1

Comparative Succinate Fermentation (Batch 2-liter at Different pH Values, Neutralization with Calcium hydroxide

|  | Ex. 1 pH 6.1 | Ex. 2 pH 6.8 |
| --- | --- | --- |
| Dextrose (Initial), g/l | 49.8 | 57.3 |
| Dextrose (Final), g/l | 0.0 | 1.6 |
| Fermentation Time, hrs. | 22.5 | 29.0 |
| Products, |  |  |
| Succinate, g | 43.5 | 20.2 |
| Acetate, g | 11.3 | 5.4 |
| Formate, g | 0.6 | 2.1 |
| Lactate, g | 0 | 39.6 |
| Succinate yield, wt (%) | 87.3 | 36.3 |
| Lactate Yield, wt (%) | 0 | 37.0 |

Fermentation Conditions:
(1) Temperature 39° C.,
(2) 1.0 atm $CO_2$ partial pressure.

EXAMPLES 3, 4 and 5

Results of batch fermentations with different partial pressures of carbon dioxide ($CO_2$) in the gas phase of fermentor are presented in Table 2. Fermentations were carried out at a controlled pH of 6.2±0.1 and the gas flow rate was 10 ml/min. Media was supplemented with 25 ppm tryptophan. Substrate fermentation and succinate yield is affected by the partial pressure of $CO_2$ in the gas phase. More substrate is fermented with an increase in the $CO_2$ partial pressure in the gas phase. Complete utilization of substrate and maximum succinate yield was only achieved when utilizing 100% $CO_2$ at atmospheric pressure in the gas phase. It is, therefore, clear that partial pressure of $CO_2$ in the gas phase is very important to achieve complete fermentation of substrate and to achieve high concentration and yield of succinate.

TABLE 2

Comparative Succinate Fermentation (Batch, 2-liter) at Different Partial Pressures of $CO_2$ in gas phase, pH Controlled at 6.2 with Calcium hydroxide

|  | Ex. 3 | Ex. 4 | Ex. 5 |
| --- | --- | --- | --- |
|  | $CO_2$ Partial Pressures | | |
|  | 0.1 atm | 0.3 atm | 1.0 atm |
| Dextrose (Initial), g/l | 48.6 | 45.2 | 47.5 |
| Dextrose (final), g/l | 33.1 | 10.2 | 0.6 |
| Fermentation Time, hrs. | 42.75 | 35.0 | 38.0 |
| Products |  |  |  |
| Succinate, g/l | 12.1 | 26.8 | 41.2 |
| Acetate, g/l | 4.7 | 9.4 | 11.5 |
| Formate, g/l | 1.3 | 3.9 | 0.5 |
| Lactate, g/l | 0.0 | 0.0 | 0.0 |
| Succinate yield, wt % | 78.1 | 76.6 | 87.8 |

Fermentation Conditions:
(1) Temperature 39° C.

EXAMPLES 6 and 7

In addition to supplying the correct pressure of $CO_2$ for a successful fermentation by *A. succiniciproducens*, the fermentation also requires the presence of sodium ions. Table 3 summarizes comparative succinate fermentation results obtained in the presence and absence of added sodium ions in the media.

TABLE 3

Comparative Succinate Fermentation (Batch, 2-liter) in Presence and Absence of Sodium Ions, pH Controlled at 6.2 with Calcium hydroxide

|  | Ex. 6 | Ex. 7 |
| --- | --- | --- |
|  | Sodium Chloride, g/l | |
|  | 0.0 | 3.5 |
| Dextrose (Initial), g/l | 47.3 | 45.4 |
| Dextrose (Final), g/l | 47.3 | 0.7 |
| Products, g/l |  |  |
| Succinate | 0.0 | 40.7 |
| Acetate | 0.0 | 10.6 |
| Formate | 0.0 | 0.6 |
| Lactate | 0.0 | 0.0 |
| Succinate yield, wt % | 0.0 | 91.0 |

Fermentation Conditions:
(1) 1.0 atm $CO_2$ partial pressure,
(2) Temperature 39° C.

Fermentation without added sodium ions produced no growth or substrate consumption. Thus, the fermentation of substrate to succinate occurred only when the appropriate quantity of sodium ions was added to the media. This was also shown by the results presented in Tables 1 and 2 when sodium ions was added as sodium carbonate to provide sodium ions as well as some dissolved carbon dioxide. These results indicated that addition of sodium ions was very critical for the start up and completion of succinate fermentation with a high yield.

When fermentations were conducted with 50-60 g/l of initial dextrose without adding tryptophan, growth of *A. succiniciproducens* was very poor. Less than 10 g/l substrate was consumed. However, with tryptophan present at 25 ppm, complete fermentation of dextrose with high yield and productivity was achieved. The results indicate that to obtain high succinate yield and complete fermentation of substrate addition of tryptophan is necessary.

EXAMPLES 8 and 9

Fed-batch fermentation

Fermentations in the fed-batch mode were conducted in 2-liter fermentors to increase the succinate concentration in the slurry for ease of recovery. A fermentation was started with a dextrose concentration of 47.8 g/l and glucose was batch fed twice (19 g/l added each feeding) during the fermentation. The concentration of corn steep liquor in the fermentation media was increased to provide a higher nutrient concentration. The medium was supplemented with tryptophan and gassed with 100% $CO_2$.

Table 4 summarizes comparative results of a batch and fed-batch fermentation. By batch feeding an additional 20 g dextrose was fermented. Due to increased substrate fermentation, a higher amount of succinate (121.8 vs 79.5 g) was recovered by filtration, while the soluble succinate concentration was not changed (approximately 14 g/l). A higher ratio (3.8) of insoluble succinate to soluble succinate was achieved in the fed batch fermentation compared to a ratio of 2.5 achieved in a batch fermentation. The succinate yield was unchanged by fed-batch fermentation. These results show that it was possible to increase the ratio of insoluble succinate to soluble succinate, thus improving the recovery process. This increase in insoluble to soluble succinate ratio was achieved by batch feeding under controlled conditions.

TABLE 4

Comparative Succinate Fermentation
(Batch vs. Fed Batch, 2-liter), pH 6.2,
Neutralized with Calcium hydroxide

|  | Ex. 8 Batch | Ex. 9 Fed-Batch |
|---|---|---|
| Dextrose (consumed), g | 54.8 | 75.3 |
| Dry solids weight, g | 79.5 | 121.8 |
| Succinate Recovered, g |  |  |
| Total | 48.5 | 66.7 |
| Solid | 34.6 | 52.9 |
| Liquid | 13.9 | 13.8 |
| Ratio of Insoluble to Soluble Succinate | 2.49 | 3.83 |
| Succinate yield (%) | 88.5 | 88.6 |
| Succinate Productivity, g/l hr | 1.9 | 1.4 |
| Products in Final Filtrate, g/l |  |  |
| Succinate | 14.4 | 14.3 |
| Acetate | 10.6 | 13.4 |
| Lactate | 0.6 | 1.5 |

Fermentation Conditions:
(1) $CO_2$ partial pressure 1 atm,
(2) Temperature 39° C.

EXAMPLE 10

Fermentation Scale up

The succinate fermentation was run in an 80-liter fermentor to confirm yield and productivity at the larger volume. Batch fermentations were carried out under 100% $CO_2$ gas phase at pH 6.2±0.1. The pH was controlled by addition of 25 wt % calcium hydroxide slurry on demand.

Table 5 summarizes the results of an 80-liter batch fermentation. Similar to 2-liter batch fermentations, complete fermentation of substrate was obtained during this large scale fermentation. A high succinate yield of 89.7 wt % was obtained, thus, achieving an improved yield over a 2-liter scale fermentation. These data showed that high yield and productivity of succinate were maintained when the fermentation was scaled to larger volumes.

TABLE 5

Succinate Fermentation (Batch, 80-liter),
pH 6.2, Neutralized with Calcium Hydroxide

|  | Ex. 10 |
|---|---|
| Dextrose (Initial), g | 2588 |
| Dextrose (final), g | 6 |
| Fermentation Volume (Initial), liter |  |
| Fermentation Time, hr. | 22.5 |
| Products, g |  |
| Succinate | 2321 |
| Acetate | 611 |
| Formate | 20 |
| Succinate yield, wt % | 89.7 |

Fermentation Conditions:
(1) $CO_2$ partial pressure 1.3 atm,
(2) Temperature 39° C.

EXAMPLE 11 and 12

Continuous Multistage Fermentation

The purpose of these fermentations was to demonstrate the succinate fermentation with simultaneous precipitation of calcium succinate in continuous multistage fermentation conditions. Fermentations were conducted at two dilution rates. In the first case the dilution rate in first stage was 0.405 $hr^{-1}$ while in the second stage it was 0.11 $hr^{-1}$. In the second case the dilution rate was changed to 0.307 $hr^{-1}$ in stage 1 and to 0.086 $hr^{-1}$ in the second stage. The results for both the cases are summarized in Table 6. Calcium succinate was precipitated in the second stage fermentor at both dilution rates. Succinate productivity was higher in stage 1 than in stage 2. Succinate yield of 85.0 wt % and productivity of 2.0 g/l hr was obtained at both dilution rates. These data indicated that a simultaneous precipitation of calcium succinate with high yield and productivity was feasible in multistage continuous fermentations.

TABLE 6

Succinate Fermentation (2-stage continuous)
at Different Dilution Rates, pH 6.2,
Neutralized with Calcium
hydroxide Slurry on Demand

|  | Ex. 11 Stage I | Ex. 12 Stage II |
|---|---|---|
| I. Dilution rate (D) | 0.405 $hr^{-1}$ | 0.11 $hr^{-1}$ |
| Dextrose (Initial), g/l | 46.3 |  |
| pH | 5.9 | 6.2 |
| At Steady State |  |  |
| Average Succinate Yield (Both Stages), wt %: | 84.9 |  |
| Average Succinate Productivity, g/l hr (Both Stages) | 2.0 |  |
| II. Dilution rate (D) | 0.307 $hr^{-1}$ | 0.086 $hr^{-1}$ |
| Dextrose (Initial), g/l | 46.7 |  |
| pH | 6.0 | 6.2 |
| At Steady State |  |  |
| Average Succinate Yield, wt %: (Both Stages) | 85.3 |  |
| Average Succinate Productivity, g/l hr (Both Stages) | 2.03 |  |

Fermentation Conditions:
(1) $CO_2$ partial pressure 1.0 atm,
(2) Temperature 39° C.

EXAMPLE 13

Fermentation with Recycle of Spent Filtrate

Fermentation with recycle of spent filtrate was conducted in 2-liter fermentors with 100% $CO_2$ in gas phase. The pH was controlled at 6.2±0.1 with 25 wt % calcium hydroxide slurry. Spent filtrate was obtained from a preceding fermentation run. Spent filtrate was added to the fermentation media in a ratio of 1:1 and nutrient additions were adjusted accordingly.

Table 7 summarizes results of a batch fermentation with recycle of filtrate. The data showed a complete fermentation of dextrose. Unexpectedly, a maximum substrate consumption rate of 5.5 g/l hr is obtained with an overall productivity of 2.3 g/l hr. Succinate yield for filtrate recycle fermentations was 87%. The spent filtrate added to the recycle fermentations contains acetate. Thus, a higher concentration of acetate was expected at the end of recycle fermentations because of the acetate initially present. The results show that a very high rate of substrate fermentation was obtained by recycling spent filtrate without any adverse effects from higher acetate concentrations. Also the media cost was lowered because nitrogenous and other soluble nutrients were recycled and less needed to be added to the fermentation media.

TABLE 7

Succinate Fermentation with Spent Filtrate Recycle at pH 6.2, Neutralized with Calcium Hydroxide

| | Ex. 13 |
|---|---|
| Dextrose (Initial), g | 49.2 |
| Dextrose (Final), g | 0.3 |
| Maximum Substrate | |
| Consumption Rate, g/l-hr | 5.5 |
| Overall Productivity, g/l-hr | 2.3 |
| Products | |
| Succinate, g | 43.0 |
| Acetate, g | 10.6 |
| Formate, g | 0.4 |
| Succinate yield (wt %) | 87.0 |

Fermentation Conditions:
(1) $CO_2$ partial pressure 1.0 atm.
(2) Temperature 39° C.

These fermentation results indicated that to achieve high succinate yield and high productivity the addition of sodium ions and tryptophan, and careful control of fermentation conditions including pH and $CO_2$ partial pressure was very important. High yield and high productivity using low cost media in conjunction with efficient recovery and purification steps are needed for an economical process. A very high succinate yield and productivity was achieved in a low cost medium irrespective of the fermentation mode (i.e. batch, fed-batch, small scale, large scale, multistage continuous) and with or without recycle of spent filtrate. Addition of spent filtrate to the fermentation up to a level of 50% did not decrease succinate yield and, in fact, increased fermentation productivity.

Product Recovery and Purification

Calcium succinate precipitate is recovered from the fermentation broth by filtration. The recovered succinate salt is then acidified using sulfuric acid and calcium sulfate is removed by filtration yielding a succinic acid stream. Finally, ion exchange treatment is used to purify the succinic acid stream. The result is a concentrated, purified succinic acid.

EXAMPLE 14

Recovery of Calcium Succinate

Simultaneous carbohydrate fermentation with precipitation of product succinate as calcium succinate was achieved in the fermentation step. The first step in concentration and purification of the succinate slurry was filtration. The filtrate and filter cake were both collected for further processing. Results of slurry filtration obtained from an 80 l batch fermentation are summarized in Table 8.

A filtration rate of 48.3 gal/hr $ft^2$ was observed for formation of a ¼" thick filter cake and a rate of 32.3 gal/hr $ft^2$ was obtained for the formation of a ½ inch thick filter cake. The cake composition obtained upon low temperature drying (non-dehydrated calcium succinate) is shown in Table 8. A portion of the nitrogenous impurity shown as protein remained in the filter cake. The filtrate collected from the filtration contained about 14 g/l succinate.

TABLE 8

Filtration of Calcium Succinate from Fermentor

| | Ex. 14 |
|---|---|
| Filtration Rates (Gal/hr $ft^2$) | |
| Total Rate to ¼ inch cake | 48.3 |
| Total Rate to ½ inch cake | 32.3 |
| Cake Composition (weight percent, dry basis) | |
| Succinate | 44.0 |
| Acetate | 2.2 |
| Protein | 3.4 |
| Calcium Carbonate | 2.1 |
| Filtrate Composition (g/l) | |
| Succinate | 13.8 |
| Acetate | 9.4 |
| Formate | 0.3 |

Conditions:
(1) Temperature 39° C.

EXAMPLE 15

Reduction of Soluble Succinate

A reduction of the soluble succinate concentration in the filtrate stream was accomplished by heating the filtrate to 80° C., allowing more calcium succinate to precipitate, followed by filtration to remove the additional calcium succinate precipitate. Table 9 shows the results collected from reheating and refiltration of succinate containing filtrate.

TABLE 9

Filtrate Heating and Refiltration Results

| | Ex. 15 |
|---|---|
| Filtration Rate (Gal/hr $ft^2$) | 20 |
| Cake Composition (weight percent, dry basis) | |
| Succinate | 35.0 |
| Acetate | 1.9 |
| Calcium carbonate | 0.0 |
| Protein | 10.5 |
| Filtrate Composition (g/l) | |
| Succinate | 9.6 |
| Acetate | 9.5 |
| Formate | 0.3 |

Conditions:
(1) Temperature 80° C.

A filtration rate of 20 gal/hr $ft^2$ was achieved for this filtration. This calcium succinate filter cake contained no carbonate impurities. Some nitrogenous material is precipitated with the cake. The residual succinate concentration in the spent filtrate was 9.6 g/l. This is lower than the succinate concentration in the feed before heating to 80° C. and shows that additional calcium succinate is removed by heating and filtration.

Table 10 shows the dry basis composition at various stages of production recovery and purification. The combined calcium succinate cake is 52.1 percent by weight succinate. The nitrogenous impurities were 5.6 percent of the calcium succinate cake.

TABLE 10

Composition of Process Streams for Succinic Acid Production
(Weight percent dry basis)

|  | Fermentation Product | Calcium Succinate Cake | After Acidification With Sulfuric Acid | After Cation Exchange Purification | After Anion Exchange Purification |
|---|---|---|---|---|---|
| Succinate | 44.5 | 52.1 | 89.6 | 91.2 | 94.2 |
| Acetate | 10.9 | 2.6 | 2.8 | 3.2 | 5.0 |
| Protein | 5.6 | 5.6 | 1.5 | 1.0 | 0.8 |
| Calcium ion | 37.3 | 36.6 | 1.6 | — | — |
| Sulfate ion | — | — | 4.5 | 4.6 | — |
| Calcium carbonate | 1.7 | 3.1 | — | — | — |

EXAMPLE 16

Conversion of Calcium Succinate to Succinic Acid

The calcium succinate filter cake was acidified with sulfuric acid, then the slurry of calcium sulfate solids (gypsum) and succinic acid solution was filtered to remove the gypsum. A quantity of sulfuric acid 10% greater than required to completely react with the calcium succinate was added to completely acidify the filter cake. After allowing time for complete reaction, the excess sulfuric acid was neutralized with calcium hydroxide. The slurry was heated to 80° C. and the gypsum was removed by filtration.

The calcium sulfate was then removed by filtration. The filtration rate was 64 gal/hr ft$^2$. The filter cake was washed with a volume of hot water equivalent to the volume of solution contained in the filter cake to remove all succinic acid. The succinic acid concentration in the soluble product, depending on the purity of the calcium succinate cake initially collected, ranged from 10% to 30% by weight.

In Table 10 the purity of the succinic acid was improved from 52.1% to 89.6% by the acidification and filtration. The calcium ion was reduced from 36.6% to 1.6% (d.b.) by the acidification and filtration process. Nitrogenous impurities (protein) were reduced from approximately 10% of the weight of succinate to 1.67% of the weight of succinate.

EXAMPLE 17

Purification of Succinic Acid by Ion Exchange

The succinic acid stream after the gypsum filtration contains calcium and other cations, sulfate and other anions, and nitrogenous impurities. Table 10 shows the composition of the stream at this point in the process.

Carefully selected ion exchange processes are used to remove the contaminating ions. Strongly acidic cation exchange resin Dowex 50WX8 (Dow Chemical Co., Midland, Mich.) in the H$^+$ cycle is used in a continuous flow column to remove the residual calcium and other cations. The succinic acid is not exchanged into this resin. Fortuitously and unexpectedly, some of the nitrogenous impurities (amino acids and proteins) are also removed along with the calcium ions (Table 10).

The product stream from the cation exchange purification step still contains anionic impurities such as sulfate (SO$_4$=) and nitrogenous impurities (proteins and amino acids). Removal of the anionic impurities from succinic acid which contained the succinate anion is a difficult task because the ion exchange sites could be saturated with the succinate anion and not remove the impurity anions. However, we have discovered that certain weakly basic anion exchange resins, among them Amberlite IRA-94 (Rohm & Haas Co., Philadelphia, Pa.), in the free base cycle are suitable for removing the impurity anions in presence of succinate anions. The resin was used in a continuous flow column. The data (Table 10) shows that the (SO$_4$=) anion impurity was removed below the assay detection level of 5 ppm whereas the succinic acid was not ion exchanged. Some of the residual nitrogenous impurities were removed and a succinic acid product containing less than one percent nitrogenous material was obtained. The aqueous stream contained 14 to 30 percent succinic acid by weight at this point in the process.

The results in Table 10 also shows that purification of the succinic acid is accomplished by using specific ion exchangers in the proper sequence. The cation exchanger must be used first followed by the anion exchanger to successfully remove the contaminants. A succinic acid product containing less than one percent nitrogenous impurity and less than 5 ppm sulfate and calcium ions is produced by the fermentation and purification process of the present invention.

The overall process will now be described in connection with the schematic process diagram of FIG. 1. Corn steep liquor, a reducing agent, if necessary, and a sodium salt are continuously heat-sterilized and blended with a fermentable carbohydrate which is fed into the blend as a continuously heat-sterilized concentrate. The blend is cooled and introduced into the first (seed) fermentor 11. The tryptophan is sterilized as required and blended with the other media components after cooling, and also fed to the seed fermentor 11. The carbon dioxide is continuously filter-sterilized and introduced into the fermentor 11. In addition, a sterile, 20–50% w/w slurry of calcium hydroxide or oxide (lime), is added to the fermentor 11 on demand for pH control.

The final media in the seed fermentor 11 consists of 25–80 g/l d.b. of carbohydrate, 5–20 g/l d.b. corn steep liquor or other complex protein source, 5–50 ppm tryptophan, and a controlled concentration of sodium salts. Once the process is under way, spent filtrate, which is recycled to the fermentor 11 constitutes 0–90% v/v of the total feed.

The optimal conditions for the fermentation depend on the microorganism selected. The preferred organism, *A. succiniciproducens*, is chosen for its high yield and high productivity at high succinate concentrations. For *A. succiniciproducens* the optimal conditions are: fermentation temperature, 32°–42° C., pH=5.8–6.6, and a positive carbon dioxide pressure (above atmospheric).

Referring back to FIG. 1, calcium hydroxide is added to the seed fermentor 11 and the main fermentor 12 on demand to maintain pH in the desired range. Carbon dioxide is added to the fermentors 11 and 12 continuously to supply $CO_2$ for metabolism and maintenance of anaerobic conditions. The carbon dioxide flow rate is 0.1 to 2.0 fermentor volumes per hour.

Figure 1:
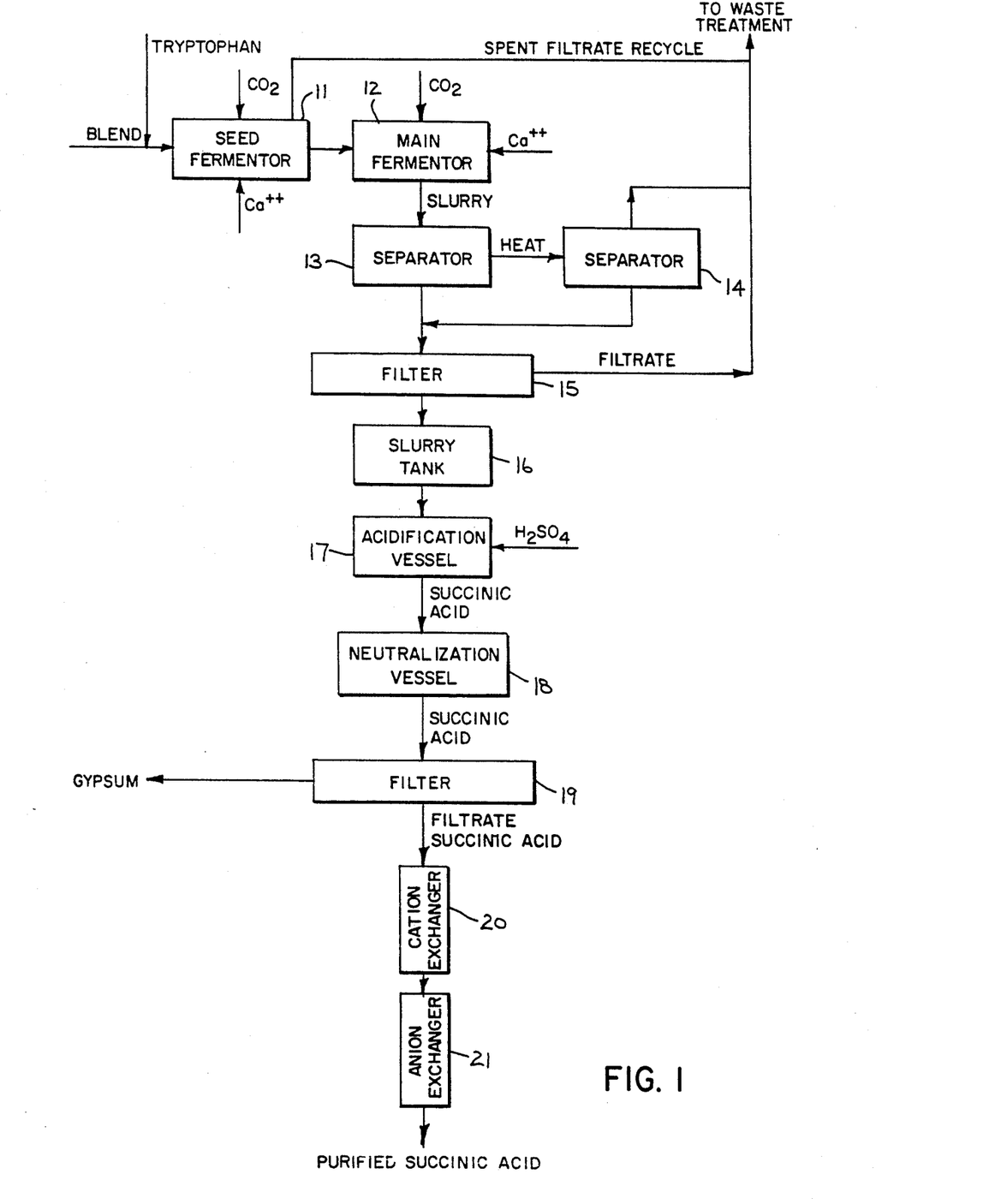

FIG. 1 shows a two-stage continuous fermentation. However, batch, fed batch and continuous fermentations have all been shown to give high yield, high productivity results. On this basis, the fermentation stage could be batch, fed batch or continuous. The fermentation stage could also be a combination of two or more configurations. The two-stage continuous configuration gives high succinate productivity with no turn around time as required between batch fermentations.

Recovery of Calcium Succinate from the Fermentation Broth

The fermentation process produces a slurry of calcium succinate in fermentation broth. The calcium succinate is concentrated and separated from the fermentation broth by filtration. The filter cake collected is washed with an equivalent volume of saturated calcium succinate solution or water, at 37° C., to remove all filtrate broth from the product cake.

Referring back to FIG. 1, in the calcium succinate recovery step the final fermentation slurry leaves the main fermentor 12 and first goes to a cyclone separator 13 or gravity settling vessel where the calcium succinate solids are separated from the supernatant liquid. The supernatant liquid is heated after it leaves the separator 13 to 70°-95° C. to precipitate more calcium succinate and the resulting slurry goes to a second separator 14. The solids from both separators 13 and 14 are combined and fed to a filter 15. There, a 30-60 wt. % succinate cake is separated from the filtrate and washed with one solids volume of a hot (70°-95° C.) calcium succinate saturated solution or a hot water stream. The wash is necessary to remove impurities from the filter cake. The filtrate is combined with the supernate from the second separator 14 and the stream is split into two portions. One portion (0-90%) of this spent filtrate is recycled back to the seed fermentor 11. The remainder of the filtrate is treated anaerobically to produce carbon dioxide and methane from the residual organic acids. The filtrate washed from the cake is recycled to the second separator 14.

The recovery of succinic acid from the calcium succinate portion of the process of FIG. 1 will now be described.

The calcium succinate filter cake is acidified with sulfuric acid to produce succinic acid and calcium sulfate. The calcium sulfate precipitates as gypsum ($CaSO_4 \cdot 2H_2O$) and is removed from the succinic acid by filtration.

On a stoichiometric basis about 5% to about 10% excess sulfuric acid is added for the acidification. After an appropriate holding time for establishing completely acidified conditions, the excess sulfuric acid is neutralized with calcium hydroxide This slurry is maintained at a temperature of 70°-95° C. and the gypsum is removed by filtration.

Referring to FIG. 1 the washed calcium succinate filter cake from the filter 15, e.g. a belt press filter, is slurried with water in a tank 16 to 20-40% w/v solids and fed to an acidification vessel 17. Concentrated sulfuric acid is slowly added in 5-10% excess to completely convert the calcium succinate in the slurry to succinic acid. The succinic acid goes into solution and calcium sulfate (gypsum) precipitates from the mixture. The residual sulfuric acid is neutralized with 40-55% industrial grade lime slurry in a neutralization vessel 18. This slurry is heated to 70°-95° C. and the precipitated gypsum is filtered through a filter 19. The filter cake is washed with its own volume of 70°-95° C. water to recover all the succinate acid and the filtrate and wash are combined. The washed gypsum cake is a by-product.

The succinic acid stream after calcium sulfate (gypsum) filtration contains calcium, sulfate, nitrogenous compounds and acetic acid as major impurities. The ion exchange treatment removes the calcium and sulfate impurities to below detectable concentrations. Some nitrogenous materials were also removed.

A strongly acidic cation exchanger, such as Dowex 50WX8, in the H+ cycle is used in a continuous flow column to remove calcium and other cations. A weakly basic anion exchanger, such as Amberlite IRA-94, in the free base cycle, is used to remove sulfate and other anionic impurities Careful control of the ion exchange process allows the anionic impurities to be removed without removing the succinic acid.

The portion of FIG. 1 relating to the purification of succinic acid by ion exchange will now be described.

The succinic acid solution from the belt press filter 19 enters a column 20 filled with strongly acidic cation exchange resin in the hydrogen cycle. Calcium and other cations are removed by this ion exchanger. The solution then passes through a weakly basic anion exchange column 21 where the resin is loaded to its limit with strong anions to avoid loss of succinic acid. This resin is in the free base cycle. Both the cation and anion resins may be regenerated by conventional methods The succinic acid product thus obtained contains less than 1% nitrogenous impurities (protein) and an undetectable concentration of cations such as calcium and anions such as sulfate.

Low impurity concentration makes this product ideal for specialty and commodity chemical uses. For conversion to commodity intermediates, the solution may be further concentrated by evaporation. Additional purity, if desired, may be obtained by crystallization, carbon absorption, electrochemical methods, esterification followed by distillation of the volatile esters. The evaporated solution may also be further heated to produce succinic anhydride which is volatile and recoverable by distillation and condensation of the anhydride.

It will be apparent to those skilled in the art that the economic production of succinic acid from carbohydrates for use in specialty and commodity chemicals, requires a fermentation process that uses low cost nutrients, produces high product concentration at a high productivity and an efficient and low-cost purification process. The novel process of the present invention meets those requirements.

The preferred microorganism *A. succiniciproducens* (ATCC 53488) grows on media containing carbohydrates, corn steep liquor, sodium ions and low concentration (25 ppm) of tryptophan. In addition, this strain has been successfully grown on a media containing spent filtrate; the use of spent filtrate was found to increase the productivity of the fermentation. This was an unexpected result because of the potential deleterious effects of cell lysing agents and accumulation of inhibitory products in the spent filtrate.

It will be apparent to those skilled in the art that various process variations can be made. Such variations may include:

i) Batch, fed batch and continuous fermentation configurations not shown in the process schematic
ii) Treatment of media to remove components not essential to the fermentation
iii) Treatment of various process streams to denature proteins and allow removal of these nitrogenous materials from the succinate streams
iv) Concentration of product by evaporation, crystallization, or membrane processes.

In summary, the process of the present invention is an innovative integration of process steps to convert low cost carbohydrates to a concentrated succinic acid product. The novel continuous process included fermentation with spent filtrate recycle and precipitation to produce a calcium succinate salt. The recovery of the succinate by filtration concentrates the insoluble succinate. The reheating of the filtrate recovers more calcium succinate precipitate from the filtrate and the recycling of the spent filtrate increases the fermentation rate. The succinic acid is recovered from the calcium succinate salt by acidification using sulfuric acid followed by filtration to remove the precipitated calcium sulfate (gypsum). Finally the removal of cation and anion impurities is accomplished by a carefully selected and operated double ion exchange process The foregoing description and examples have been for purposes of illustration only and the invention is not to be limited except by the claims.

REFERENCES

1. Guerrant, G. O., et al., *J. Clinical Microbiol.*, v. 16, (2), 355, (1982).
2. Fronson, M. A., ed., "Sulfate Analysis", Method No. 426A, in: *Standard Methods*, (16th), Amer. Chem. Soc., Washington, D.C. 464 (1985).
3. Howlett, et al., *Applied & Environ. Microbiol.*, 32, 274-283, (1976).
4. Caldwell, et al., *J. Bacteriol.*, 98, 668-76 (1969).
5. Hamlin, et al., *J. Bacteriol.*, 72, 548-54.
6. Anderson & Ordal, *J. Bacteriol.*, 81, 139 (1969).
7. Caspari, et al., *Arch. Microbiol.*, 135, 16-24 (1983)
8. Bouchard, E. F. & E. G. Merritt, "Citric Acid", In: vol. 6, *Encyclopedia of Chemical Technology*, H. F. Mark, et al., eds., John Wiley & Sons, N.Y., 150-79 (1979).
9. Van Ness, J. H., "Hydroxy Carboxylic Acids", In: vol. 13, *Encyclopedia of Chemical Technology*, H. F. Mark, et al., eds., John Wiley & Sons, N.Y., 80-103 (1981).
10. Winstrom, L. O., "Succinic Acid & Succinic Anhydride", In: vol. 21, *Encyclopedia of Chemical Technology*, H. F. Mark, et al., eds., John Wiley & Sons, N.Y., 848-865 (1983).
11. Datta, R. and C. J. Lemme, Eur. Patent Appl. EP O 249 773, Dec. 23, 1987.

We claim:

1. A process for the production and purification of succinate, said process comprising:
   (a) growing an anaerobic succinate producing microorganism which has all the identifying characteristics of *Anaerobiospirillum succiniciproducens* ATCC No. 53488 in a fermentor on a medium containing at least 20 g/l of assimilable carbohydrate and other required nutrients under anaerobic conditions at a pH of 5.8 to 6.4 in the presence of sodium ions and dissolved carbon dioxide in equilibrium with a partial pressure of at least 0.1 atmosphere of carbon dioxide; and
   (b) adding calcium oxide or calcium hydroxide during the fermentation to maintain the pH of the fermentation broth in the range of 5.8 to 6.4 and to precipitate the succinate as calcium succinate from the broth.

2. A process of claim 1 in which the fermentation is conducted on a batch basis.

3. A process of claim 1 in which the fermentation is conducted on a fed batch basis.

4. A process of claim 1 in which the fermentation is conducted on a continuous basis.

5. The process of claim 1 which further comprises filtering the fermentation broth to collect the precipitated calcium succinate.

6. The process of claim 5 which further comprises heating the filtrate to precipitate additional calcium succinate and, if desired, recycling the resulting filtrate back to the fermentor.

7. The process of claim 5 which further comprises:
   (a) forming an aqueous slurry of the calcium succinate and adding sulfuric acid to it to form a reaction mixture containing insoluble calcium sulfate and soluble succinic acid;
   (b) filtering the reaction mixture to remove insoluble calcium sulfate and to obtain an aqueous phase containing succinic acid and any soluble cation and anion impurities;
   (c) treating the aqueous phase first with a strongly acidic cation exchanger in the free acid form to remove any cation impurities; and
   (d) then treating the solution with a weakly basic anion exchanger in the free base form to remove any strong anion impurities to obtain a succinic acid product of high purity which contains less than about 1% nitrogenous impurities.

* * * * *